United States Patent [19]
Ahonen et al.

[11] Patent Number: 5,323,777
[45] Date of Patent: Jun. 28, 1994

[54] SENSOR POSITION INDICATOR COILS TO BE USED IN MAGNETOENCEPHALOGRAPHIC EXPERIEMNTS AND A MEANS OF ATTACHING THEM TO THE HEAD

[75] Inventors: Antti I. Ahonen; Matti S. Hämäläinen, both of Helsinki; Pasi P. Laine, Espoo; Visa A. Vilkman, Helsinki, all of Finland

[73] Assignee: Neuromag Oy, Finland

[21] Appl. No.: 783,856

[22] Filed: Oct. 28, 1991

[30] Foreign Application Priority Data

Nov. 1, 1990 [FI] Finland ................................. 905397

[51] Int. Cl.$^5$ .............................................. A61B 5/05
[52] U.S. Cl. .................. 128/653.1; 128/731; 324/248
[58] Field of Search ....................... 128/653.1, 731, 630, 128/640, 644; 324/244, 248, 249

[56] References Cited

U.S. PATENT DOCUMENTS

| | | | |
|---|---|---|---|
| 4,697,598 | 10/1987 | Bernard et al. | 128/731 |
| 4,709,702 | 12/1987 | Sherwin | 128/731 |
| 4,749,946 | 6/1988 | Hoenig | 324/248 |
| 4,793,355 | 12/1988 | Crum et al. | 128/653.1 |
| 4,967,038 | 10/1990 | Gevins et al. | 128/731 |
| 5,038,782 | 8/1991 | Gevins et al. | 128/731 |

FOREIGN PATENT DOCUMENTS

| | | |
|---|---|---|
| 0199214 | 10/1986 | European Pat. Off. . |
| 0399499 | 11/1990 | European Pat. Off. . |
| 2124704 | 11/1972 | Fed. Rep. of Germany . |
| 2206913 | 3/1973 | Fed. Rep. of Germany . |
| 2315498 | 10/1973 | Fed. Rep. of Germany . |
| 3135962 | 5/1982 | Fed. Rep. of Germany . |
| 3148192 | 6/1983 | Fed. Rep. of Germany . |

OTHER PUBLICATIONS

CRC Critical Reviews in Biomedical Engineering, vol. 14, Iss 2 pp. 93-126, (1986), "Cerebral Magnetic Field", Hari et al.
Journal of Low Temperature Physics, vol. 76, Iss 5/6, pp. 287-386 (1989) "SQUID Magnetometers for Low Frequency Applications", Ryhanen et al.
Review of Scientific Instruments, vol. 58, Iss 11, pp. 2145-2156 (1987), "Large-area low-noise seven-channel dc SQUID magnetometer for brain research", Knuutila et al.
Advances in Biomagnetism, pp. 689-692 and 693-696 (1989).
IEEE Transactions on Magnetics, vol. MAG-17, iss 1, pp. 400-401 (1981).

*Primary Examiner*—Lee S. Cohen
*Assistant Examiner*—Krista M. Pfaffle
*Attorney, Agent, or Firm*—Andrus, Sceales, Starke & Sawall

[57] ABSTRACT

Sensor position indicator coils to be used in magnetoencephalographic experiments and a means of attaching them to the head. The invention comprises a headband (1) and a coil assembly attached to it. The coil assembly consists of a coil set (5) and of at least three fastening strips (6) or of fastening strips having coil sets of individual coils (5') on them. The mechanical properties of the coils are very important. The coil set (5) has three thin- or thick-film coils cast in epoxy resin. The outside surface of the headband (1) and the inside surfaces of the fastening strips (6) have been covered with materials adhering to each other easily. In addition, the underside of the coil set (5) can contain three small knobs, formed during casting, on which the coil set leans when pressed against the head, staying in the tangent plane of the head.

9 Claims, 5 Drawing Sheets

SENSOR POSITION INDICATOR COILS TO BE USED IN MAGNETOENCEPHALOGRAPHIC EXPERIEMNTS AND A MEANS OF ATTACHING THEM TO THE HEAD

BACKGROUND OF THE INVENTION

This invention is about coils used in magnetoencephalographic experiments to determine the position and orientation of the magnetometer, and a means of attaching the said coils to the head. In magnetoencephalography (MEG), the weak magnetic fields elicited by the human brain are measured. The method is gaining gradually a more important role in medical research and diagnostics. In particular, it is possible to investigate the brain functions and disorders in a human being without touching the person or exposing him to electromagnetic radiation or radioactive tracers. In contrast to the widely used electroencephalogram (EEG), in which the electric potential distribution is measured on the surface of the scalp, the magnetoencephalogram suffers far less from distortions caused by inhomogeneities in the conductivity of the human tissue. Therefore, it is possible to locate source currents related to brain activity with a spatial and temporal resolution of a few millimeters and milliseconds. The method has been reviewed in detail, for example, in CRC Critical Reviews in Biomedical Engineering, volume 14 (1986), issue 2, pp. 93–126.

Instruments used in MEG should be able to detect magnetic signals whose magnetic flux density is typically 100 fT or less. In addition, the measurement is to be performed simultaneously at several locations; the measurement of even more than one hundred magnetic signals from all over the head is necessary. The only sensor capable of detecting these minute signals is the so-called Superconducting Quantum Interference Device (SQUID) magnetometer. The operation of the device has been explained in detail in an article in Journal of Low Temperature Physics, volume 76 (1989), issue 5/6, pp. 287–386.

In order to locate accurately the current distribution caused by the brain's activity from the measured magnetic field distribution, the position and orientation of the magnetometers with respect to the head has to be known. Mechanical means of determining the position and orientation are too elaborate and prone to errors; therefore an automatic position indicator system is needed.

In magnetoencephalographic experiments, one typically uses a locating method employing at least three transmitter coils which are attached to the subject's head; the positions and orientations of the coils are accurately determined prior to the measurement by some other means. The system also includes a current supply, a magnetic field detector, and a computer to determine the coordinates of the coils on the basis of the measured magnetic field. The system is capable of automatically determining the position and orientation of the magnetometer during the measurement. As the magnetic detector of the position indicator system, a multichannel SQUID-magnetometer is particularly useful (cf. Review of Scientific Instruments, volume 58 (1987), issue 11, pp. 2145–2156 or Advances in Biomagnetism, edited by S. J. Williamson, M. Hoke, G. Stroink, and M. Kotani, Plenum Press, New York 1989, pp. 689–692 and pp. 693–696). Another known position indicator system U.S. Pat. No. 4,793,355 employs orthogonal coil sets comprising three coils as transmitters and receivers; the method is based on the induction principle. The receiver coils are attached to the head of the subject and the transmitter coils to the magnetometer.

It is crucial for the accuracy of the position indication that the coils stay firmly on their positions during the measurement; it is also important to have them as close to the measurement area as possible. Usually, the coils are wound, by hand or by other means, from wire around a non-magnetic core, as in the references cited above. Three such coils are cast in epoxy resin, forming a coil set. The coil sets are attached to the subject's head by means of a flexible headband or with adhesive tape.

The main drawback of the prior-art technique is that the coil sets are too big to be attached to the actual measurement area, i.e. between the head and the SQUID magnetometer. On the other hand, the present techniques do not provide a possibility to attach the coils firmly at an arbitrary position on the cortex. When using a headband, the area where the attachment of the coils is possible is limited, and the hair prevents a firm adhering of the coils with tape. The accuracy of dimensions of wire-wound multi-turn coils is not very good, and taking into account the stray fields or eliminating them is very elaborate. The determination of the effective dipole moment of the coil is therefore difficult; the error reflects itself correspondingly in the results of the sensor position determination.

In another context, several possible means of attaching the coils to the head have been described. For example, DE-2 206 913 deals with a stiff headband to be placed around the subject's head for attaching EEG electrodes. The headband is hinged on the back, and it is tightened around the head using a punched rubber strap or, alternatively, a spring-loaded hinge. The electrodes are attached to the headband via stiff connector wires. The wires are bent in a spring-like manner to press the electrodes against the head.

The solution presented in the said reference has several drawbacks. Due to the completely stiff structure, the construction cannot be made flat enough not to considerably hamper the ease of operation of the magnetometer. As a result, the multichannel magnetometer must be placed rather far from the head, resulting in a substantially deteriorated signal-to-noise ratio. In addition, the means of attaching the electrodes (FIG. 1 of the reference cited above) is not suitable for position indicator coils because it utilizes only one support arm: a well-defined position and orientation (along the tangent plane) on the head, accurate enough for the MEG method and stationary during the measurement, cannot be guaranteed; coils may move easily during the measurement, for instance, when moving the magnetometer. A third drawback is that the electrodes can only be attached to certain predetermined positions.

DE-2 124 704 describes an elastic, hollow headband used to attach electrodes. The electrodes are located on the inside surface of the headband, and when the headband is pressurized, e.g., by compressed air the electrodes are pressed against the head of the subject. This is not a solution either, because the construction cannot be made flat enough not to hamper the placing the magnetometer as close to the head as possible. In addition, the electrodes can be attached only to predetermined places.

In EP-A2-399 499 magnetometer elements are attached to a stiff shell (cf. FIG. 6 of the reference). The method is not suitable for position indicator coils, since the resulting structure is completely stiff. The coils cannot be attached freely anywhere on the cortex on every subject so that the distance from the magnetometers to the head would not substantially increase. A solution to this problem would be an individual, tight-fitting shell for each subject, but this would certainly considerably annoy the subject. In addition, making individual shells would make clinical measurements with patients more elaborate and increase the time consumption and cost for preparing the measurement excessively.

EP-A3-199 214 mentions two means of attaching electrodes to the subject's head. The first one employs an elastic cap which can be set very tightly against the head. The second method includes a stiff headband which can be tightened around the head. A stiff strip is then attached to this headband in a fixed and stiff manner; this strip goes over the head. Neither of the two methods is suitable for position indicator coils, since the elastic cap does not guarantee that the coils are not moved during the measurement and the stiff construction does not allow a free selection of measurement points on the cortex. The stiff construction is also uncomfortable for the subject.

The use of planar coils, fabricated using thin film or thick film techniques and encapsulating them inside epoxy resin as well as the use of parallel conductors patterned on flexible, insulating substrates is known as such, for example, from DE-A1-3 135 962, DE-C3-2 315 498, U.S. Pat. No. 4,749,946 Transactions on Magnetics, vol. MAG-17, issue 1 (January 1981), pp. 400–401 and DE-A1-3 148 192. None of the features described in the above references solves alone the problem how to make a small, dimensionally accurate coil the stray fields of which are negligible, including current supply leads, and which is, in addition, as flat as possible and can be reliably and easily attached to the head.

SUMMARY OF THE INVENTION

With the present invention, a substantial improvement to the prior art is gained. The features heretofore characteristic to this invention are described in the appended claims.

The most important advantage of the invention is that the position indicator coils can be firmly and easily attached to the head without sacrificing the free choice of the place of attachment or the comfort of the subject. In addition, the coil set can be made so thin that it fits without any trouble between the subject's head and the magnetometer. The fastening strips made of a thin, non-stretching and flexible material, wide enough to prevent lateral movements, guarantee that the coils stay in place during the measurement and firmly press the coils against the head.

The use of planar coils fabricated with thin- or thick film techniques, combined with the use of the headband and the fastening strips, described in the appended claims, in a common structure is the key to functionality of the concept. The planar coils can be made very thin, and with the use of cast epoxy resin the coils and their necessary contact leads can be encapsulated to protect them mechanically for increased reliability and to attach the coils to the fastening strips. At the same time, the cast epoxy resin can be used to form the small elevations or knobs necessary for supporting the coil element. The fastening strips also include the current supply leads; when the return conductors run symmetrically on both sides of the supply conductor, the stray fields due to them are minimized.

BRIEF DESCRIPTION OF THE DRAWING

In the following, the invention is described in detail, with reference to the attached drawings.

DESCRIPTION OF THE PREFERRED EMBODIMENT

Figure 1:
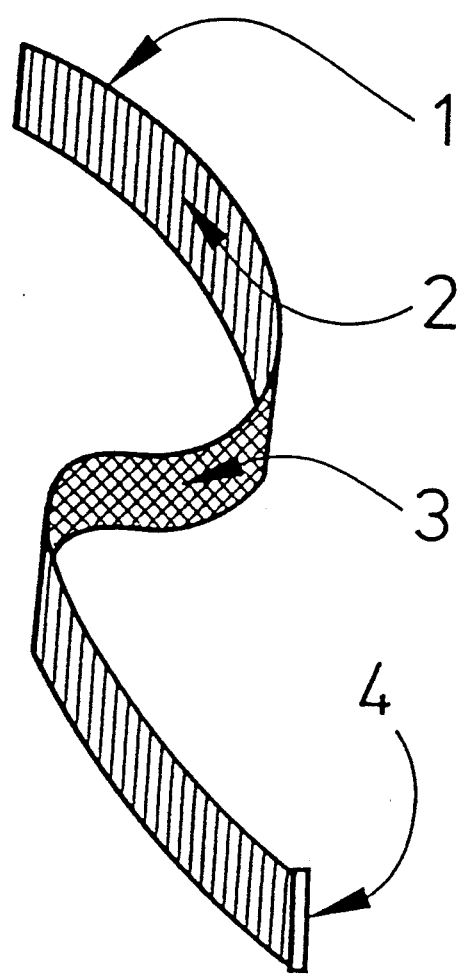
FIG. 1 represents the headband portion and FIG. 2a the coil portion so that the part against the head is visible.

The headband (1) shown in FIG. 1 is made of fabric or other similar material and its inside has been covered with material (2), which glides poorly on the skin, e.g. thin foam plastic.

Figure 2A:
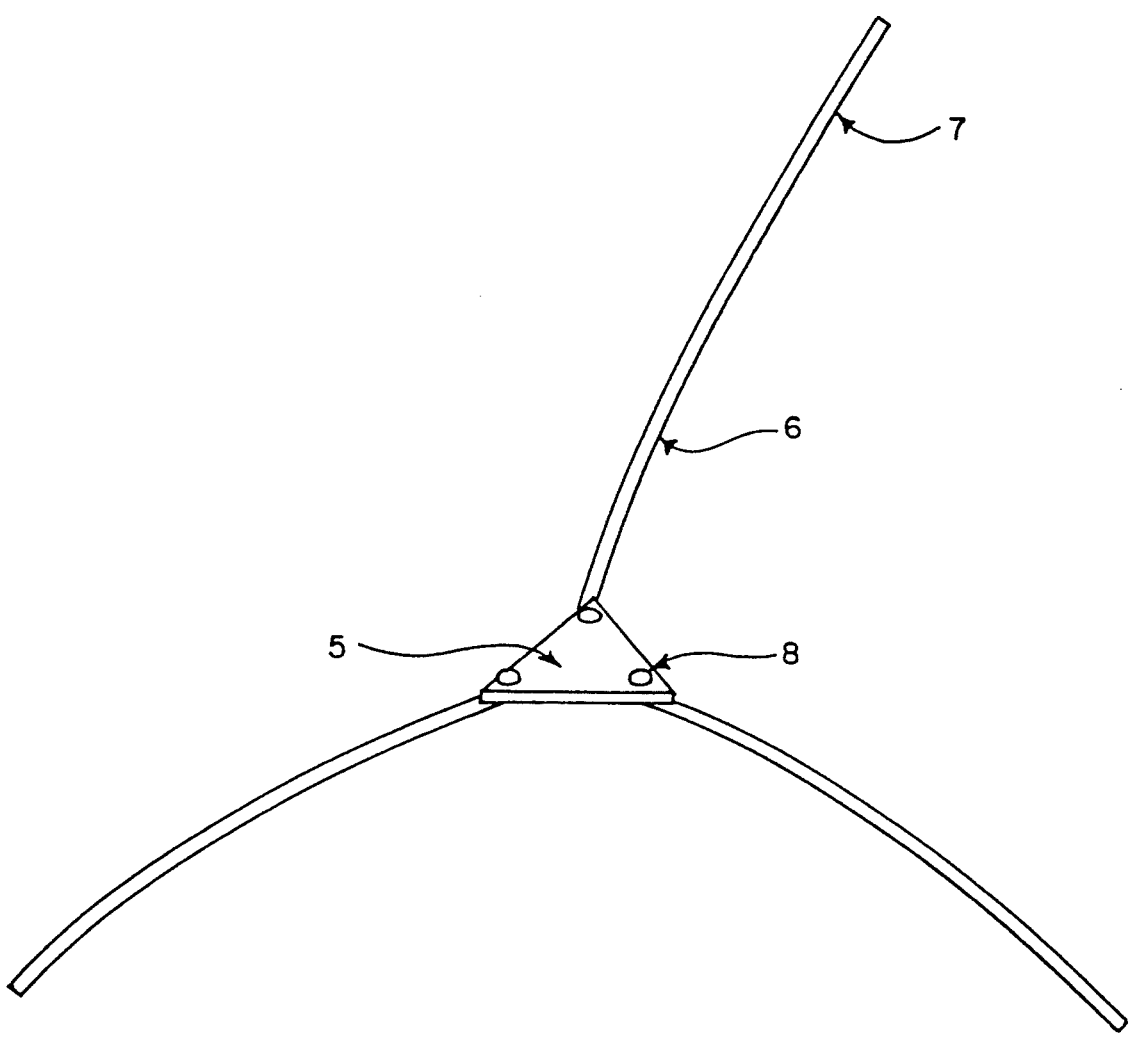
In FIG. 2b, an alternative embodiment of the coils portion is shown.
Figure 2B:
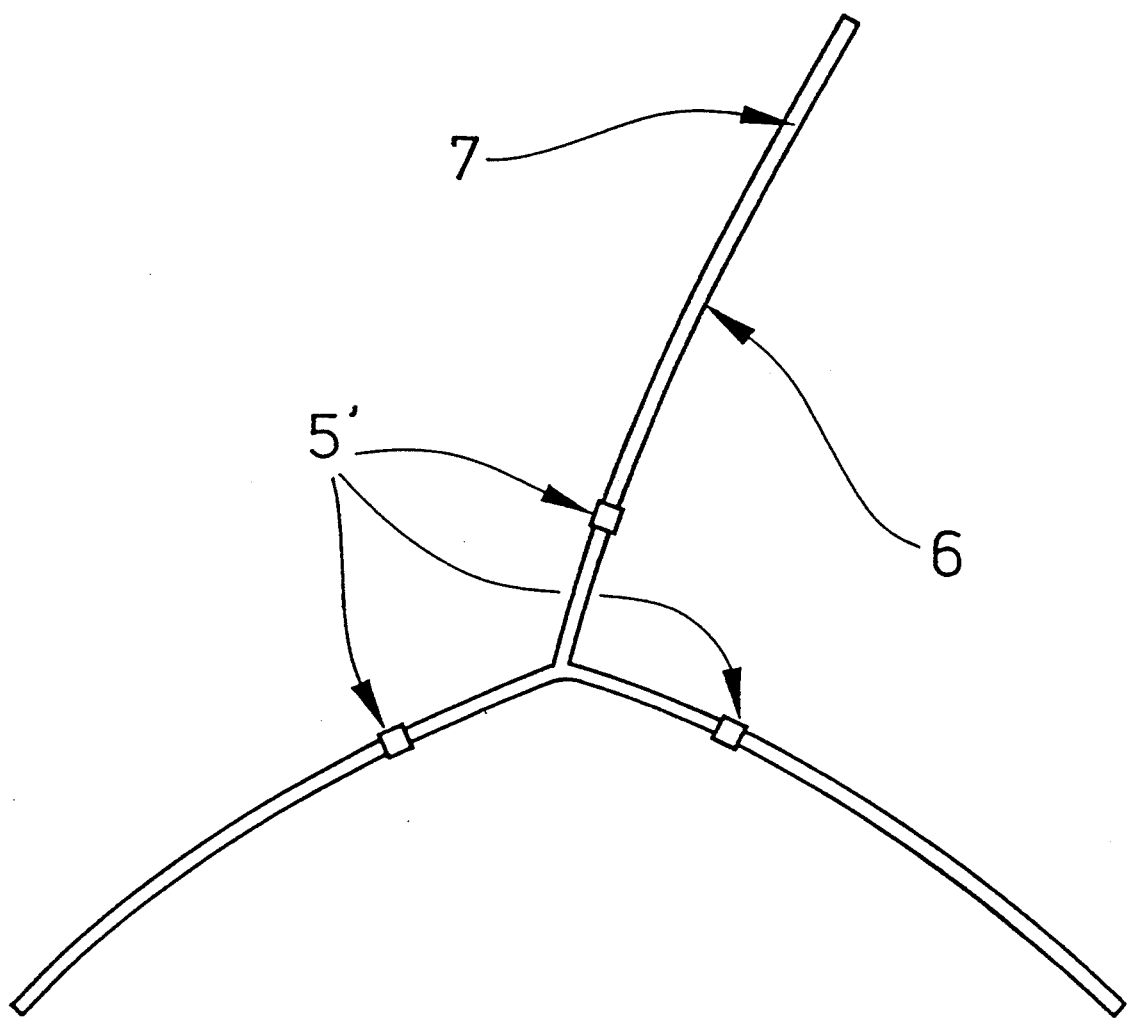

The outside surface of the headband has been covered with material (3) onto which the fastening strips of the coil assembly, shown in FIG. 2a and FIG. 2b, adhere. This can be accomplished using, e.g. commercially available Velcro TM tape, which has a plurality of small hooks. In addition, the headband has a buckle (4) or another similar device with which the headband is fixed firmly around the head.

The coil assembly, depicted in FIG. 2a, comprises the planar coil set (5) attached to at least three long enough fastening strips (6) made of a thin, flexible and non-stretchable material, e.g. fiber glass. In an alternative embodiment (FIG. 2b) each of the fastening strips has a planar coil set (5) or a separate planar coil (5').

The strips ought to be so thin that they bend easily following the curvature of the head but, at the same time, thick enough to exert a force sufficient to press the coils against the head. In addition, the strips must be wide enough to prevent bending laterally. The underside of the strips has been covered with material (7) adhering to the outside surface of the head band, such as Velcro TM tape. In addition, the coil set has at least three small elevations (8) so that the coil set will settle firmly in the tangent plane of the head, leaning on the knobs (8).

Figure 3:
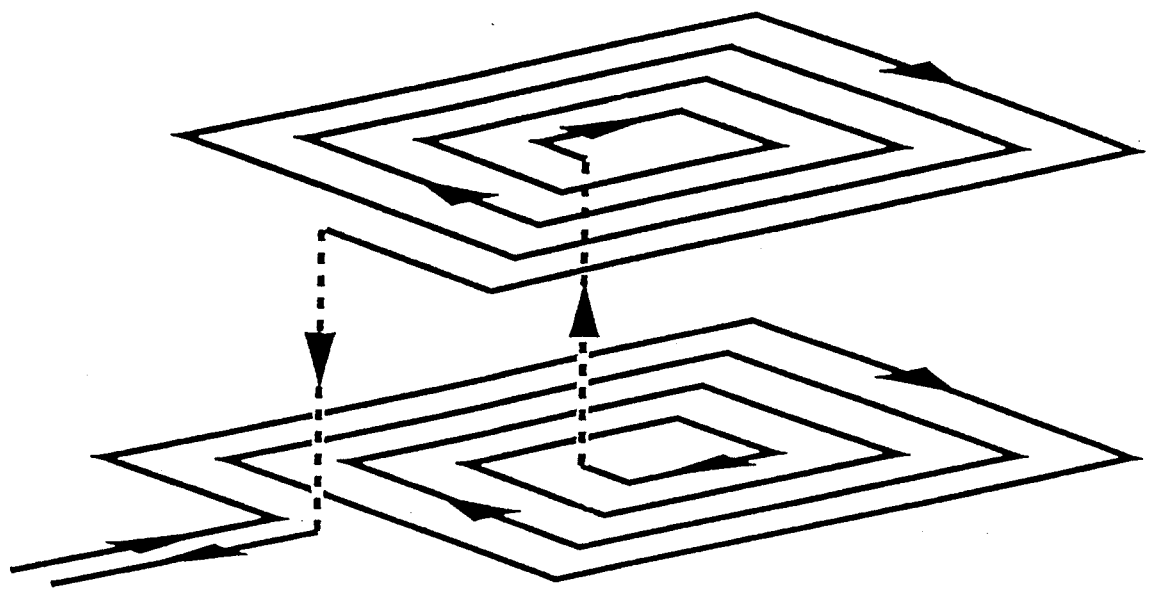
In FIG. 3, the geometry of the coil is shown schematically.

The coil set (5) comprises at least three coils fabricated using thin or thick film techniques. Also, the separate coils (5') have been made with the same methods. Each coil consists of, for example, of two spirals laid on top of each other so that the spirals are mirror images. Then, the current can be routed from one spiral to another simply by a connector in the insulating material in between. The magnetic fields of the two spirals add to each other, and the stray fields of the conductors can be minimized by having the conductors on top of each other on the substrate plane. FIG. 3 shows this situation. The supply leads to the coils should be made as twisted pairs or coaxial cables to minimize stray fields. The embodiment, where the current supply leads have been patterned with a printed-circuit board technique on the fastening strips, is especially preferable. The stray fields can be minimized in that case so that the middle conductor is symmetrically surrounded by two return conductors. The coils are contacted with the supply leads using, for example, ultrasonic bonding and thin contact wires. The coils with the contacts can finally be encapsulated in epoxy resin or other cast plastics. A coil assembly so fabricated has a thickness of only a few millimeters.

Figure 4:
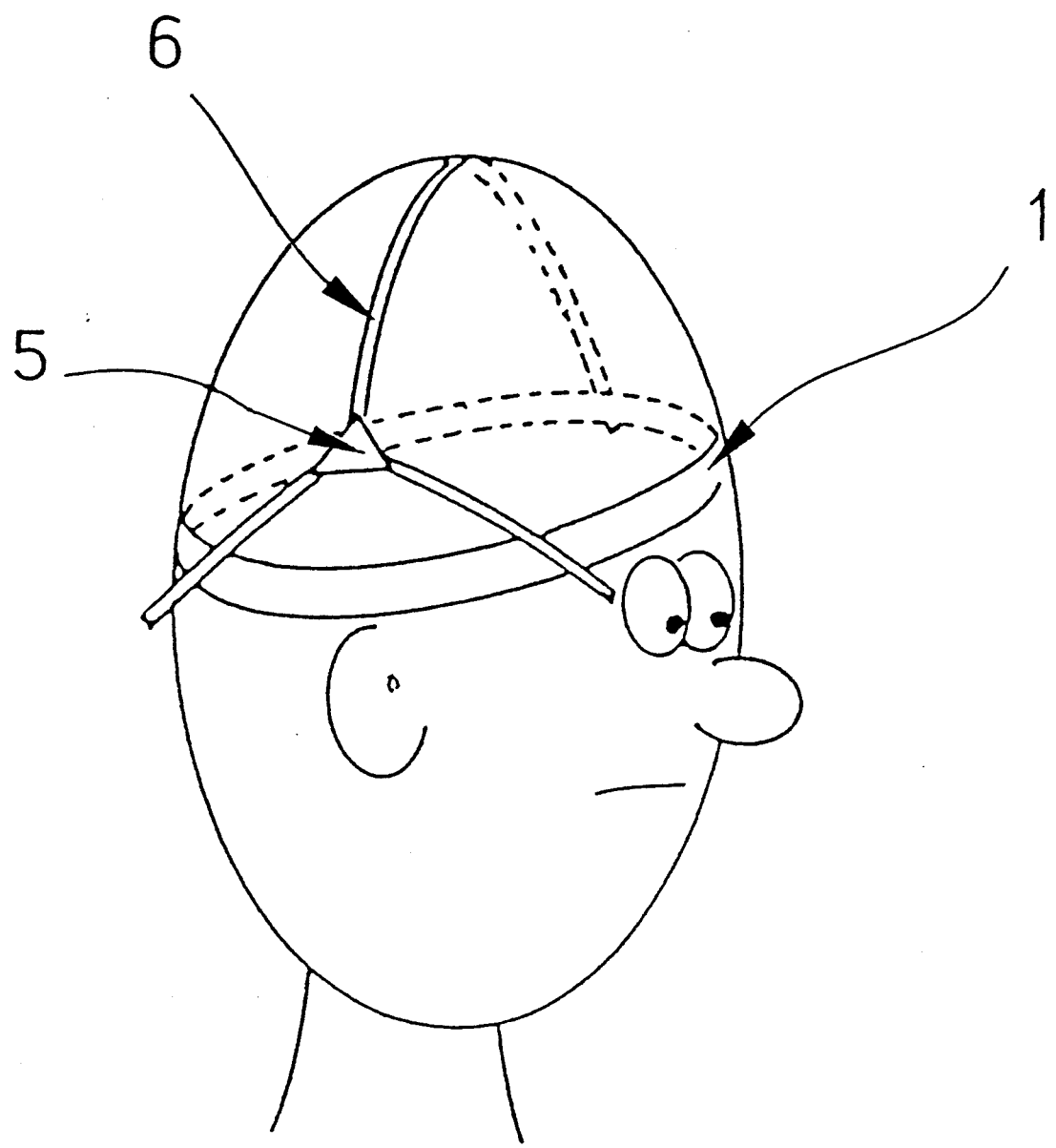
FIG. 4 represents the invention attached to the head of the subject.

When using the invention, the headband shown in FIG. 1 is first set firmly around the head. Thereafter, the coil assembly is positioned to the desired place and the fastening strips are pressed, following tightly the shape of the head, on the headband. FIG. 4 shows the invention attached to the head. The knobs of the coil set, penetrating through hair, are leaning against the head to keep the coils firmly in place and oriented in the tangent plane of the head. The properties of the fastening strips described earlier guarantee that the coils are pressed against the head and that the coil set cannot move during the measurement in any direction. Analogously, when removing the coils form the head, the fastening strips are first detached from the headband and thereafter the headband is loosened.

Especially, the fastening strips need not be of equal length. For example, when using three strips one of the strips can be made longer than the others, facilitating the connection to the headband that is most far apart. The strips can be equipped with extensions, too.

We claim:

1. Sensor position indicator coil apparatus for use in magnetoencephalography employing sensors on the surface of the head of a subject, said apparatus comprising:
   a headband (1) adapted to be fixed around the head of the subject, said headband conforming to the shape of the head;
   coil means (5, 5') for indicating sensor position, said coil means having at least one coil formed of a conductive film on a substrate; and
   at least three thin, flexible, non-stretchable fastening strips (6) connected to said coil means, said strips being releasibly engaged with said headband for positioning said coil means at an arbitrary desired location on the head of the subject;
   said headband and said strips having abuttable surfaces containing means for releasibly engaging said strips with said headband.

2. Sensor position indicator coil apparatus according to claim 1 wherein said coil means comprises a single planar coil set (5).

3. Sensor position indicator coil apparatus according to claim 2 wherein said coil means has at least three small, spaced, elevations on a side of said coil means which is applied to the head of the subject for positioning said coil means generally in a condition of tangency to the surface of the head to which the coil means is applied.

4. Sensor position indicator coil apparatus according to claim 2 wherein one of said fastening strips contains a conductive film in which current leads for said coil means are formed, said current leads comprising a center conductor extending along said strip and carrying current in one direction and return conductors on either side of said center conductor for carrying current in the opposite direction, whereby stray fields are minimized.

5. Sensor position indicator coil apparatus according to claim 1 wherein said coil means comprises a plurality of coil sets (5'), one of which is attached to each of said fastening strips.

6. Sensor position indicator coil apparatus according to claim 5 wherein each of said fastening strips contains a conductive film in which current leads for said coil means are formed, said current leads comprising a center conductor extending along said strip and carrying current in one direction and return conductors on either side of said center conductor for carrying current in the opposite direction, whereby stray fields are minimized.

7. Sensor position indicator coil apparatus according to claim 1 wherein the fastening strips (6) each have a width dimension along which the abuttable surface of said strip lies and a thickness dimension normal to said width dimension, said thickness dimension being such that the strips may be bent over the surface of the head and exert forces that press said coil means against the head when so bent, and said width dimension being such that bending of said strips in a direction parallel to said width dimension is prevented.

8. Sensor position indicator coil apparatus according to claim 1 wherein said coil means has electrical contacts for current leads to said coil means, and wherein said coil means, said electrical contacts, and portions of said strips adjacent said coil means are encapsulated in a resin.

9. Sensor position indicator coil apparatus according to claim 1 wherein at least one of said fastening strips contains a conductive film in which current leads for said coil means are formed, said current leads comprising a center conductor extending along said strip and carrying current in one direction and return conductors on either side of said center conductor for carrying current in the opposite direction, whereby stray fields are minimized.

* * * * *